United States Patent
Wiemker et al.

(10) Patent No.: US 11,348,229 B2
(45) Date of Patent: May 31, 2022

(54) DETERMINING REGIONS OF HYPERDENSE LUNG TISSUE IN AN IMAGE OF A LUNG

(71) Applicant: KONINKLIJKE PHILIPS N.V., Eindhoven (NL)

(72) Inventors: Rafael Wiemker, Hamburg (DE); Axel Saalbach, Hamburg (DE); Jens Von Berg, Hamburg (DE); Tom Brosch, Hamburg (DE); Tim Philipp Harder, Ahrensburg (DE); Fabian Wenzel, Hamburg (DE); Christopher Stephen Hall, Kirkland, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 40 days.

(21) Appl. No.: 16/644,037

(22) PCT Filed: Sep. 4, 2018

(86) PCT No.: PCT/EP2018/073711
§ 371 (c)(1),
(2) Date: Mar. 3, 2020

(87) PCT Pub. No.: WO2019/048418
PCT Pub. Date: Mar. 14, 2019

(65) Prior Publication Data
US 2021/0065361 A1    Mar. 4, 2021

Related U.S. Application Data

(60) Provisional application No. 62/554,197, filed on Sep. 5, 2017.

(30) Foreign Application Priority Data

Sep. 22, 2017 (EP) .................................... 17192665

(51) Int. Cl.
*G06T 7/00* (2017.01)
*G06T 7/11* (2017.01)
(Continued)

(52) U.S. Cl.
CPC ............ *G06T 7/0012* (2013.01); *A61B 6/032* (2013.01); *A61B 6/50* (2013.01); *G06T 7/11* (2017.01);
(Continued)

(58) Field of Classification Search
CPC . G06T 7/0012; G06T 7/11; G06T 7/70; G06T 2207/30008; G06T 2207/30048;
(Continued)

(56) References Cited

U.S. PATENT DOCUMENTS 7,397,937 B2    7/2008   Schneider et al.
8,417,009 B2    4/2013   Mizuno
(Continued)

FOREIGN PATENT DOCUMENTS

EP    1315125 A2    5/2003
WO    2015177723 A1    11/2015

OTHER PUBLICATIONS

International Search Report and Written Opinion, International Application No. PCT/EP2018/073711, dated Dec. 20, 2018.
(Continued)

*Primary Examiner* — Vu Le
*Assistant Examiner* — Julius Chai
(74) *Attorney, Agent, or Firm* — Micah-Shalom Kesselman

(57) ABSTRACT

There is provided a computer-implemented method and system (100) for determining regions of hyperdense lung parenchyma in an image of a lung. The system (100) comprises a memory (106) comprising instruction data representing a set of instructions and a processor (102)
(Continued)

configured to communicate with the memory and to execute the set of instructions. The set of instructions, when executed by the processor (102), cause the processor (102) to locate a vessel in the image, determine a density of lung parenchyma in a region of the image that neighbours the located vessel, and determine whether the region of the image comprises hyperdense lung parenchyma based on the determined density, hyperdense lung parenchyma having a density greater than −800 HU.

14 Claims, 7 Drawing Sheets

(51) Int. Cl.
| | | |
|---|---|---|
| *G06T 7/70* | (2017.01) | |
| *A61B 6/03* | (2006.01) | |
| *A61B 6/00* | (2006.01) | |
| *G06V 10/44* | (2022.01) | |
| *G06V 10/50* | (2022.01) | |

(52) U.S. Cl.
CPC .............. *G06T 7/70* (2017.01); *G06V 10/457* (2022.01); *G06V 10/507* (2022.01); *G06T 2207/30008* (2013.01); *G06T 2207/30048* (2013.01); *G06T 2207/30061* (2013.01); *G06T 2207/30101* (2013.01); *G06V 2201/03* (2022.01)

(58) Field of Classification Search
CPC . G06T 2207/30061; G06T 2207/30101; G06T 2207/10081; G06T 2207/10104; G06T 2207/10088; A61B 6/032; A61B 6/50; G06K 9/4638; G06K 9/4647; G06K 2209/05
See application file for complete search history.

(56) References Cited

U.S. PATENT DOCUMENTS

| | | | |
|---|---|---|---|
| 9,471,989 B2 | 10/2016 | O'Dell | |
| 2005/0207630 A1 | 9/2005 | Chan et al. | |
| 2006/0018524 A1 | 1/2006 | Suzuki et al. | |
| 2006/0056691 A1* | 3/2006 | Vaz | G06T 15/08 382/173 |
| 2006/0247510 A1* | 11/2006 | Wiemker | G06T 7/155 600/407 |
| 2007/0177785 A1* | 8/2007 | Raffy | G16H 30/20 382/131 |
| 2008/0137921 A1* | 6/2008 | Simon | G06T 7/11 382/128 |
| 2010/0189337 A1* | 7/2010 | Jandt | A61B 6/504 382/132 |
| 2010/0296709 A1* | 11/2010 | Ostrovsky-Berman | G06T 7/11 382/128 |
| 2011/0243403 A1 | 10/2011 | Mizuno | |
| 2014/0355858 A1* | 12/2014 | O'Dell | G06T 7/11 382/131 |
| 2015/0078641 A1* | 3/2015 | Tan | G06T 7/12 382/131 |
| 2017/0039711 A1 | 2/2017 | Dincer et al. | |
| 2017/0206662 A1* | 7/2017 | Wang | G06T 7/143 |

OTHER PUBLICATIONS

Jia, T. et al., "A novel lung nodules detection scheme based on vessel segmentation on CT images", Bio-Medical Materials and Engineering, 2014.

De Nunzio, G et al., "Automatic Lung Segmentation in CT Images with Accurate Handling of the Hilar Region", Journal of Digital Imaging, vol. 24, No. 1, Feb. 2011.

Cressoni, M et al., "Limits of normality of quantitative thoracic CT analysis", Critical Care, 2013.

Edwards, R. et al., "A Quantitative Approach to Distinguish Pneumonia From Atelectasis Using Computed Tomography Attenuation", J Comput Assist Tomogr. Sep.-Oct. 2016;40(5):746-51.

O. Ecabert, J. Peters, H. Schramm, C. Lorenz, J. von Berg, M. J. Walker, Ma. Vembar, M. E. Olszewski, K. Subramanyan, G. Lavi, J. Weese, "Automatic Model-based Segmentation of the Heart in CT Images" IEEE Transactions on Medical Imaging 2008, 27(9), 1189-1201.

D. Lesage, E D. Angelini, L Bloch, G. Funka-Lea, A review of 3D vessel lumen segmentation techniques: Models, features and extraction schemes, Medical Image Analysis, vol. 13 (6), 2009, p. 819-845.

Wiemker R, Klinder T, Bergtholdt M, Meetz K, Carlsen IC, Bülow T, A radial structure tensor and its use for shape-encoding medical visualization of tubular and nodular structures. IEEE Trans Vis Comput Graph. 2013, vol. 19(3), p. 353-66.

Maduskar Pragnya et al.: "Automatic Detection of Pleural Effusion in Chest Radiographs", Medical Image Analysis, vol. 28 , pp. 22-32, XP029372424.

* cited by examiner

DETERMINING REGIONS OF HYPERDENSE LUNG TISSUE IN AN IMAGE OF A LUNG

This application is the U.S. National Phase application under 35 U.S.C. § 371 of International Application No. PCT/EP2018/073711, filed on 4 Sep. 2018, which claims the benefit of European Application Serial No. 17192665.2, filed 22 Sep. 2017 and U.S. Provisional Application No. 62/554,197, filed 5 Sep. 2017. These applications are hereby incorporated by reference herein.

FIELD OF THE INVENTION

This disclosure relates to the field of image processing and, in particular, to a method and system for determining regions of hyperdense lung tissue in an image of a lung.

BACKGROUND TO THE INVENTION

Healthy lung parenchyma is usually of very low density, close to air (−800 HU). Diseased non-aerated lung tissue, on the other hand, can be denser than water (>0 HU). Certain diseases such as pneumonia and atelectasis (collapsed tissue) manifest as hyperdense regions of lung tissue, where the density is greater than aerated lung tissue. It is thus beneficial to identify these hyperdense regions.

In an existing technique, hyperdense regions are identified by manually sampling density values from hyperdense pulmonary areas. However, this manual sampling technique is time consuming, and suffers from reproducibility issues, both of which present barriers to the use of the technique in clinical practice. For this reason, the automatic sampling of density values from hyperdense pulmonary areas is of high interest.

However, the automated detection of hyperdense regions of the lung can be challenging, particularly since hyperdense regions of the lung are not recognised by standard lung segmentation algorithms due to their atypical high densities. This can lead to poor (or failed) lung segmentation, which reduces the effectiveness of automated methods. Furthermore, hyperdense parenchyma manifests with similar densities to pleural effusions (diseased areas of the lung that are filled with water) and thus, even when a hyperdense region is detected, it can be challenging to determine whether it is hyperdense parenchyma or a pleural effusion.

The paper entitled "A Quantitative Approach to Distinguish Pneumonia From Atelectasis Using Computed Tomography Attenuation" by Edwards et al., 2016, discusses methods to distinguish between pneumonia and atelectasis in medical images, when a hyperdense region of parenchyma has been located in a lung. However, the paper does not address the problems highlighted above associated with detecting hyperdense regions in the first place.

There is thus a need for an improved method and system for determining regions of hyperdense lung tissue in an image of a lung.

US 2017/039711 A1 discloses a system and method for detecting central pulmonary embolisms in a subject's vasculature is provided. In some aspects, the method includes receiving, using the input, a set of images representing a vasculature of the subject's lungs, automatically analyzing the set of images to segment the main arteries associated with the subject's lungs and separate the main arteries from surrounding tissues. The method also includes automatically extracting central pulmonary embolism candidates from the set of images after segmenting and separating the main arteries, and automatically evaluating the central pulmonary embolism candidates in three-dimensional (3D) space by applying a series of rules. The method further includes automatically displaying a report indicating evaluated central pulmonary embolism candidates on a display.

EP 1 315 125 A2 discloses a method and system for lung disease detection. US 2011/243403 A1 discloses a medical image processing apparatus and method, and computer readable recording medium on which is recorded program for the same. US 2006/018524 A1 discloses a computerized scheme for distinction between benign and malignant nodules in thoracic low-dose CT. US 2005/207630 A1 relates to lung nodule detection and classification.

SUMMARY OF THE INVENTION

As noted above, there are various challenges associated with automatically locating and identifying hyperdense regions of lung parenchyma using image processing. In particular, there are problems associated with segmenting images of diseased lungs due to atypical lung densities caused by disease. It is also challenging to quickly and accurately determine whether a hyperdense region comprises hyperdense parenchyma or pleural effusion. It would thus be valuable to improve the automated identification of hyperdense parenchyma and provide a system and method that overcomes some of these problems.

Therefore according to a first aspect, there is provided a system configured for determining regions of hyperdense lung parenchyma in an image of a lung. The system comprises a memory comprising instruction data representing a set of instructions. The system further comprises a processor configured to communicate with the memory and to execute the set of instructions. When executed by the processor, the set of instructions cause the processor to locate a vessel in the image, determine a density of lung parenchyma (in terms of Hounsfield units, HU) in a region of the image that neighbours the located vessel, and determine whether the region of the image comprises hyperdense lung parenchyma based on the determined density (hyperdense lung parenchyma having a density greater than −800 HU).

Hyperdense lung tissue comprises vascular structures, whereas pleural effusions are merely water-filled pockets. By locating a vessel in the image and looking for hyperdense lung tissue (hyperdense lung parenchyma) in regions that neighbour the located vessel, any hyperdense regions that are determined (or identified) by the system are therefore more likely to be regions of hyperdense lung parenchyma as opposed to pleural effusions. Effectively, the system can use vessels as markers about which to search for hyperdense lung tissue (such as hyperdense lung parenchyma). By concentrating on regions around vessels, the system may also determine the locations of hyperdense parenchyma more computationally efficiently than methods that indiscriminately scan the full lung. Areas of the lung without vessels (that are more likely to be pleural effusions) are inherently avoided and this reduces the number of false-positive detections of hyperdense lung parenchyma. A density may be determined by analyzing the intensity values of the pixels of which the image consists, in case of a 2D-image, or of the voxels of which the image consists, in case of a 3D-image. A density or radiodensity of the lung tissue or lung parenchyma may be determined from the value associated with the image component using a predetermined relationship. Hence, the density of the lunge tissue or lung parenchyma in a region can be determined based on the values associated with the image components in said region.

In some embodiments, causing the processor to determine a density of lung parenchyma in the region may comprise causing the processor to determine the density of lung parenchyma in a region of the image that surrounds the located vessel.

In some embodiments, the image may comprise a plurality of image components, and the determined density of lung parenchyma in the region may be a distribution of density values of the image components in the region.

In some embodiments, the distribution of density values may comprise a histogram of density values of the image components in the region.

In some embodiments, if the region is determined to comprise hyperdense lung parenchyma, the set of instructions, when executed by the processor, may further cause the processor to identify a medical condition associated with the hyperdense lung parenchyma using a distribution of density values in the region of the image that neighbours the located vessel.

In some embodiments, the set of instructions, when executed by the processor, may further cause the processor to determine a location of a bone in the image and determine that hyperdense lung parenchyma is absent in the region if the region overlaps the determined location of the bone.

In some embodiments, the set of instructions, when executed by the processor, may further cause the processor to determine a location of a hyperdense region in the image, and determine that the hyperdense region comprises pleural effusion if the location of the hyperdense region lies outside the region of the image that neighbours the located vessel.

In some embodiments, a region may be determined to comprise hyperdense lung parenchyma where the density of the lung parenchyma in the region is greater than an average density of aerated lung parenchyma.

In some embodiments, the average density of aerated lung parenchyma may be approximately −800 Hounsfield units (HU).

In some embodiments, causing the processor to locate a vessel in the image may comprise causing the processor to segment the image to locate one or more portions of the heart, identify, from the segmentation, a stump of a vessel (corresponding to a portion of the vessel that leaves the heart) and locate the vessel in the image using the stump as a starting point.

In some embodiments, the image may comprise a plurality of image components and causing the processor to locate a vessel in the image may comprise causing the processor to, for each image component in a region surrounding the stump, determine a measure that is indicative of the likelihood that the image component comprises part of the vessel and locate a further portion of the vessel from the location of the stump and the determined measures.

In some embodiments, causing the processor to locate the vessel in the image may further comprise causing the processor to iteratively (for each further portion of the vessel that is located), for each image component in a region surrounding the further portion of the vessel, determine a measure that is indicative of the likelihood that the image component comprises part of the vessel and locate another further portion of the vessel from the determined measures.

In some embodiments, the processor may be caused to locate a vessel in the image with a diameter that is less than a predefined threshold diameter.

According to a second aspect, there is provided a computer-implemented method for determining regions of hyperdense lung parenchyma in an image of a lung. The method comprises locating a vessel in the image, determining a density of lung parenchyma in a region of the image that neighbours the located vessel, and determining whether the region of the image comprises hyperdense lung parenchyma based on the determined density (hyperdense lung parenchyma having a density greater than −800 HU).

According to a third aspect, there is provided a computer program product comprising a computer readable medium, the computer readable medium having computer readable code embodied therein, the computer readable code being configured such that, on execution by a suitable computer or processor, the computer or processor is caused to perform the method as described above.

There is thus provided an improved method and system for determining regions of hyperdense lung tissue (hyperdense lung parenchyma) in an image of a lung, which overcomes the existing problems.

BRIEF DESCRIPTION OF THE DRAWINGS

For a better understanding of embodiments, and to show more clearly how they may be carried into effect, reference will now be made, by way of example only, to the accompanying drawings, in which.

DETAILED DESCRIPTION OF THE EMBODIMENTS

As noted above, there is provided an improved method and system for determining regions of hyperdense lung tissue in an image of a lung, which overcomes the existing problems.

Figure 1:
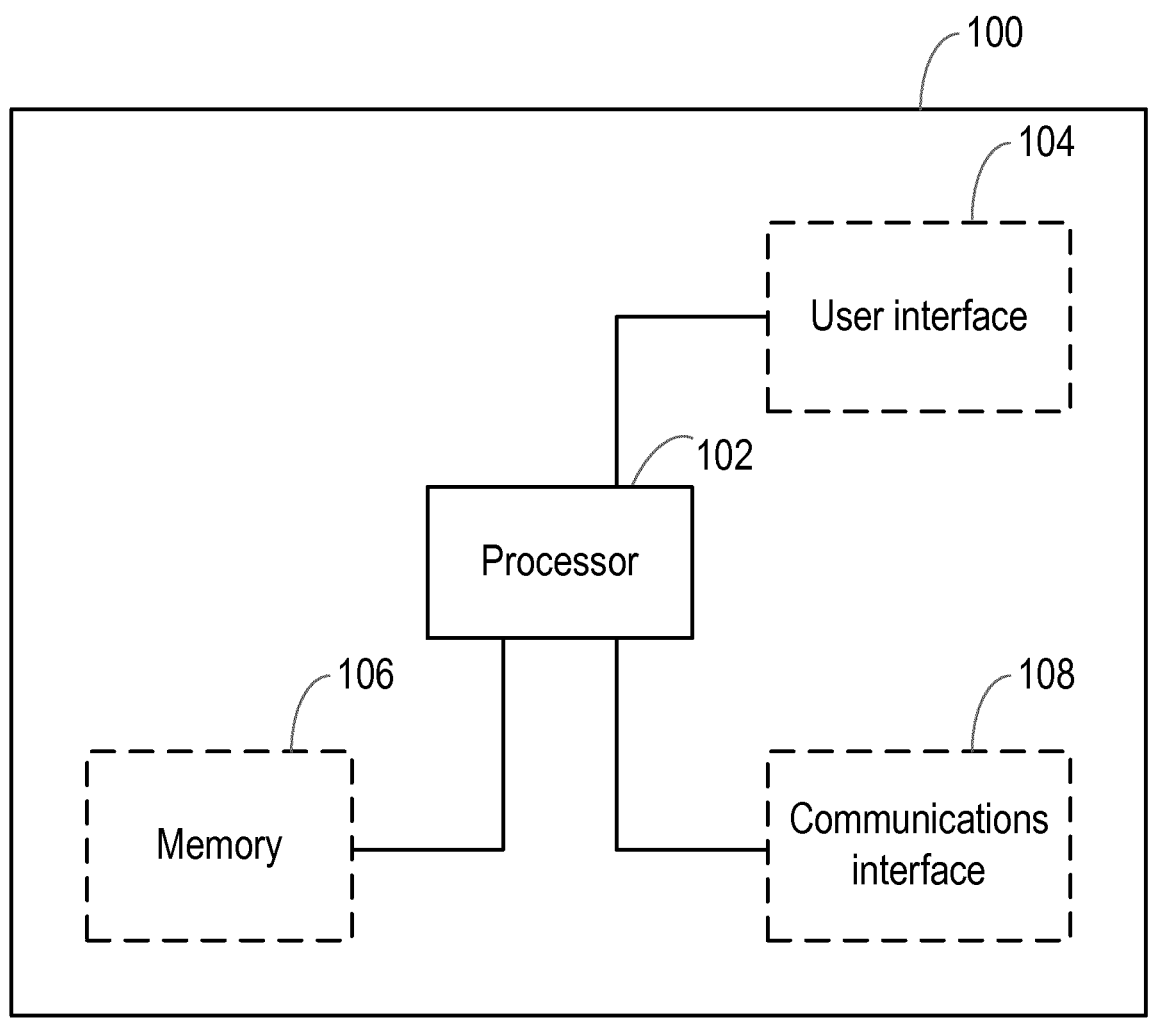
FIG. 1 is a block diagram of a system for determining regions of hyperdense lung tissue in an image of a lung according to an embodiment.

FIG. 1 shows a block diagram of a system 100 according to an embodiment that can be used for determining (e.g. locating) regions of hyperdense lung tissue in an image of a lung. With reference to FIG. 1, the system 100 comprises a processor 102 that controls the operation of the system 100 and that can implement the method described herein.

The system 100 further comprises a memory 106 comprising instruction data representing a set of instructions. The memory 106 may be configured to store the instruction data in the form of program code that can be executed by the processor 102 to perform the method described herein. In some implementations, the instruction data can comprise a plurality of software and/or hardware modules that are each configured to perform, or are for performing, individual or multiple steps of the method described herein. In some embodiments, the memory 106 may be part of a device that also comprises one or more other components of the system 100 (for example, the processor 102 and/or one or more other components of the system 100). In alternative embodiments, the memory 106 may be part of a separate device to the other components of the system 100.

In some embodiments, the memory 106 may comprise a plurality of sub-memories, each sub-memory being capable of storing a piece of instruction data. In some embodiments where the memory 106 comprises a plurality of sub-memories, instruction data representing the set of instructions may be stored at a single sub-memory. In other embodiments where the memory 106 comprises a plurality of sub-memories, instruction data representing the set of instructions may be stored at multiple sub-memories. For example, at least one sub-memory may store instruction data representing at least one instruction of the set of instructions, while at least one other sub-memory may store instruction data representing at least one other instruction of the set of instructions. Thus, according to some embodiments, the instruction data representing different instructions may be stored at one or more different locations in the system 100. In some embodiments, the memory 106 may be used to store images, information, data, signals and measurements acquired or made by the processor 102 of the system 100 or from any other components of the system 100.

The processor 102 of the system 100 can be configured to communicate with the memory 106 to execute the set of instructions. The set of instructions, when executed by the processor may cause the processor to perform the method described herein. The processor 102 can comprise one or more processors, processing units, multi-core processors and/or modules that are configured or programmed to control the system 100 in the manner described herein. In some implementations, for example, the processor 102 may comprise a plurality of (for example, interoperated) processors, processing units, multi-core processors and/or modules configured for distributed processing. It will be appreciated by a person skilled in the art that such processors, processing units, multi-core processors and/or modules may be located in different locations and may perform different steps and/or different parts of a single step of the method described herein.

Briefly, the set of instructions, when executed by the processor 102 of the system 100 cause the processor 102 to locate a vessel in an image of a lung, determine a density of lung tissue in a region of the image that neighbours the located vessel and determine whether the region of the image comprises hyperdense lung tissue based on the determined density.

In some embodiments, the set of instructions, when executed by the processor 102 may also cause the processor 102 to control the memory 106 to store images, information, data and determinations related to the method described herein. For example, the memory 106 may be used to store the image of the lung, the location of the located vessel in the image of the lung, the determined density of lung tissue in a region of the image that neighbours the located vessel and/or information pertaining to the determination of whether the region of the image comprises hyperdense lung tissue.

In any of the embodiments described herein, the image can be a two-dimensional image, a three-dimensional image, or any other dimensional image. The image may comprise a plurality (or set) of image components. In embodiments where the image is a two-dimensional image, the image components are pixels. In embodiments where the image is a three-dimensional image, the image components are voxels.

The image can, for example, be a medical image, or any other type of image, of a lung. The images may be acquired using any imaging modality. Examples of a medical image include, but are not limited to, a computed tomography (CT) image (for example, from a CT scan) such as a C-arm CT image, a spectral CT image or a phase contrast CT Image, an x-ray image (for example, from an x-ray scan), a magnetic resonance (MR) image (for example, from an MR scan), an ultrasound (US) image (for example, from an ultrasound scan), fluoroscopy images, nuclear medicine images, or any other medical image of a lung. Although examples have been provided for the type of image, a person skilled in the art will appreciate that the teachings provided herein may equally be applied to any other type of image of a lung.

As mentioned earlier, the image generally comprises an image of a lung. For example, the image may comprise lung tissue, vascular structures associated with the lung (for example, vessels in the lung) and/or portions of bones surrounding the lung such as at least a portion of one or more rib bones. The image may further comprise other anatomical structures, such as the heart and/or vascular structures that extend from the heart. It will be appreciated that the image may not necessarily comprise the entire lung and may, for example, only comprise part of a lung and/or, if other anatomical structures are present in the image, part(s) of the other anatomical structures.

As used herein, the term 'tissue' is generally used to refer to parenchyma that forms part of the lung. For example, tissue may comprise portions of the lung involved in gas transfer such as the alveoli, alveolar ducts and respiratory bronchioles. Tissue may further comprise vasculature associated with the lung. As used herein, the term 'hyperdense lung tissue' is used to describe any lung tissue having a density greater than healthy aerated lung tissue. Healthy aerated lung tissue typically has a low density that is comparable to that of air, which has a density of −800 HU (Hounsfield units). Hyperdense lung tissue may therefore be defined as lung tissue having a density greater than about −800 HU (for example, greater than −800 HU). As will be familiar to a person skilled in the art, the Hounsfield scale is a quantitative scale for describing radiodensity (e.g. the ability of electromagnetic radiation to pass through a material). The output of computed tomography (CT) scanners, for example, are typically calibrated onto the Hounsfield scale, with reference to water which has a value of 0 HU.

Returning again to FIG. 1, in some embodiments, the system 100 may comprise at least one user interface 104. In some embodiments, the user interface 104 may be part of a device that also comprises one or more other components of the system 100 (for example, the processor 102, the memory 106 and/or one or more other components of the system 100). In alternative embodiments, the user interface 104 may be part of a separate device to the other components of the system 100.

A user interface 104 may be for use in providing a user of the system 100 (for example, a medical personnel, a healthcare provider, a healthcare specialist, a care giver, a subject, or any other user) with information resulting from the method according to embodiments herein. The set of instructions, when executed by the processor 102 may cause processor 102 to control one or more user interfaces 104 to provide information resulting from the method according to embodiments herein. For example, the set of instructions, when executed by the processor 102 may cause the processor 102 to control one or more user interfaces 104 to render (or output or display) any individual one or any combination of: the image of the lung, a visual representation of the located vessel in the image of the lung, the determined density of lung tissue in a region of the image that neighbours the located vessel and/or information pertaining to the determination of whether the region of the image comprises hyperdense lung tissue.

Alternatively or in addition, a user interface 104 may be configured to receive a user input. In other words, a user interface 104 may allow a user of the system 100 to manually enter instructions, data, or information. The set of instructions, when executed by the processor 102 may cause processor 102 to acquire the user input from one or more user interfaces 104.

A user interface 104 may be any user interface that enables rendering (or output or display) of information, data or signals to a user of the system 100. Alternatively or in addition, a user interface 104 may be any user interface that enables a user of the system 100 to provide a user input, interact with and/or control the system 100. For example, the user interface 104 may comprise one or more switches, one or more buttons, a keypad, a keyboard, a touch screen or an application (for example, on a tablet or smartphone), a display screen, a graphical user interface (GUI) or other visual rendering component, one or more speakers, one or more microphones or any other audio component, one or more lights, a component for providing tactile feedback (e.g. a vibration function), or any other user interface, or combination of user interfaces.

In some embodiments, as illustrated in FIG. 1, the system 100 may also comprise a communications interface (or circuitry) 108 for enabling the system 100 to communicate with interfaces, memories and/or devices that are part of the system 100. The communications interface 108 may communicate with any interfaces, memories and devices wirelessly or via a wired connection.

It will be appreciated that FIG. 1 only shows the components required to illustrate this aspect of the disclosure and, in a practical implementation, the system 100 may comprise additional components to those shown. For example, the system 100 may comprise a battery or other power supply for powering the system 100 or means for connecting the system 100 to a mains power supply.

Figure 2:
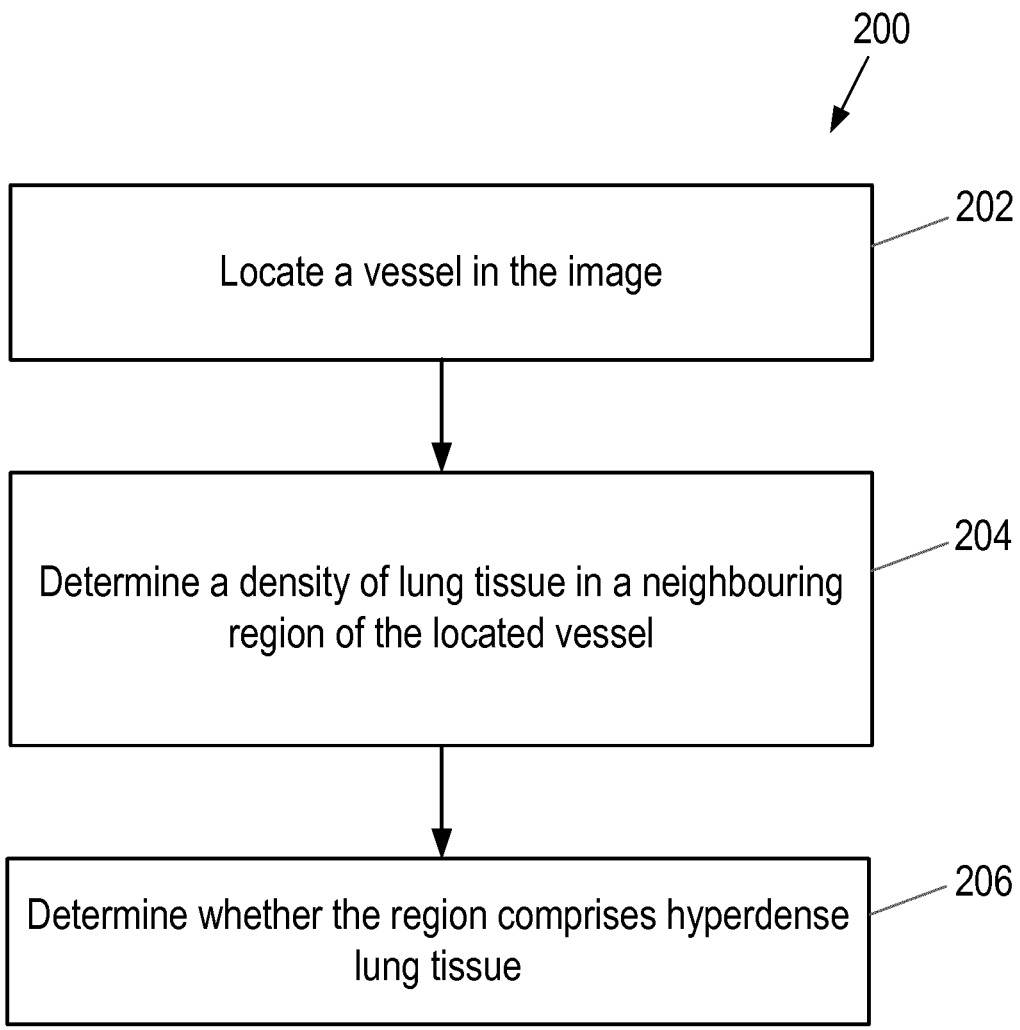
FIG. 2 illustrates a computer-implemented method for determining regions of hyperdense lung tissue in an image of a lung according to an embodiment.

FIG. 2 illustrates a computer-implemented method 200 for determining (e.g. locating) regions of hyperdense lung tissue in an image of a lung according to an embodiment. The illustrated method 200 can generally be performed by or under the control of the processor 102 of the system 100. The method may be partially or fully automated according to some embodiments.

Briefly, with reference to FIG. 2, the method comprises locating a vessel in the image (at block 202 of FIG. 2), and determining a density of lung tissue in a region of the image that neighbours the located vessel (at block 204 of FIG. 2). The method also comprises determining whether the region of the image comprises hyperdense lung tissue based on the determined density (at block 206 of FIG. 2).

As noted earlier, it can be difficult to distinguish whether hyperdense regions comprise hyperdense lung tissue or pleural effusions in images because the regions may have similar densities. In view of the fact that hyperdense lung tissue comprises vascular structures, whereas pleural effusions are merely water filled pockets, the method 200 of FIG. 2 overcomes some of the aforementioned difficulties by determining a density of lung tissue in a region of the image that neighbours a located vessel (for example, sampling areas of lung tissue that are associated with vascular structures and are therefore more likely to comprise hyperdense lung tissue). This is more computationally efficient than methods that indiscriminately scan the full lung for hyperdense lung tissue. The method 200 of FIG. 2 enables hyperdense lung tissue (such as hyperdense lung parenchyma) to be determined or identified, rather than pleural effusion since pleural effusions are inherently avoided because they do not comprise vessels. This reduces the number of false-positive detections of hyperdense lung tissue.

In more detail, at block 202 of FIG. 2, a vessel is located in an image of a lung. More specifically, the set of instructions, when executed by the processor 102 of the system 100, cause the processor 102 to locate the vessel in the image of the lung. The image of the lung may be acquired by the processor 102 from imaging equipment (such as medical imaging equipment). For example, in an embodiment where the image is a computed tomography (CT) image, the processor 102 may acquire the CT image of the lung from a CT scanner. Similarly, for example, in an embodiment where the image is an x-ray image, the processor 102 may acquire the x-ray image of the lung from an x-ray machine. In some embodiments, the image of the lung may be stored in the memory 106 (which may, for example, be a memory of a database, a server, or any other memory). For example, the processor 102 may download the image of the lung from the memory 106.

In effect, by locating a vessel in the image of the lung, the vessel can be used as a marker with which to locate regions that may comprise hyperdense lung tissue. Generally, the vessel may be a lung vessel associated with the vascular structure of the lung or a vessel associated with the vascular structure of another anatomical structure, such as the heart or any other vascular structure, or any combination of vascular structures. In some embodiments, the vessel may be an artery or vein. In some embodiments where the vessel is associated with the vascular structure of the lung, the vessel may be a principle pulmonary artery or vein, such as, for example, the left or right pulmonary arteries or the right superior, right inferior, left superior or left inferior veins.

The vessel may be located in the image in any suitable manner. For example, the vessel may be located by way of a user input acquired by the processor 102 of the system 100. Alternatively, the vessel may be located using a computer-implemented method for determining the location of a vessel in an image. The computer-implemented method for determining the location of a vessel in an image can, for example, be based on detected structures in the image. In some embodiments, the vessel can be located in the image through the use of image segmentation. This can be performed using any segmentation technique suitable for use in locating the vessel in the image and the person skilled in the art will be familiar with various segmentation methods that might be used. However, as an example, the image segmentation that can be used in locating the vessel in the image may comprise a model-based image segmentation. The skilled person will be familiar with model-based segmentation. However, briefly, model-based segmentation comprises fitting a model of an anatomical structure to an anatomical structure in an image. Thus, in this case, a model of the lung may be fitted to the lung in the image. Models used in model-based segmentation can comprise, for example, a plurality of points (such as a plurality of adjustable control points), where each point of the model may correspond to a different point on the surface of the anatomical structure. Appropriate models may comprise meshes comprising a plurality of segments, such as a polygon mesh comprising a plurality of polygon segments (for example, a triangular mesh comprising a plurality of triangular segments or any other polygon mesh). The skilled person will be familiar with such models and appropriate model-based image segmentation processes.

In some embodiments, a vessel may be located (or traced) in the image with reference to a known starting point of a vessel in the image. The geometry of anatomical structures (such as the heart) and the stumps of vessels that correspond to portions of the vessels that leave the anatomical structures are well known and can be used as starting points from which to locate the vessel in the image. For example, the geometry of the heart and the stumps of the principle pulmonary arteries and veins (such as the first few centimetres of the arteries or veins as they leave the heart) are well known and can be used as starting points from which to locate the vessel in the image.

To this end, in some embodiments, locating a vessel in the image can comprise causing the processor 102 of the system 100 to segment the image to locate one or more portions of the heart and identifying, from the segmentation, a stump of a vessel (where, as noted above, the stump of a vessel corresponds to a portion of the vessel that leaves the heart). The vessel can then be located in the image using the stump as a starting point. The heart may be segmented, for example, by determining the approximate position of the heart in the image (for example, using any suitable feature extraction technique such as a Generalized Hough Transform (GHT), or any other feature extraction technique) and then segmenting the heart using any of the segmentation methods mentioned earlier. For example, in some embodiments, a model of the heart in the form of a mesh (such as a mesh comprising a plurality of segments, which may be triangular segments or any other polygon segments) may be fitted to the heart in the image. In some embodiments, the model of the heart may also be adapted to the heart in the image, such as in an iterative fashion, for example, using trained edge detectors. The model of the heart may comprise one or more aforementioned vessel stumps, and thus once the heart in the image is segmented using the model, the position of the vessel stumps in the image are known from the segmentation, e.g. because the portion of the model corresponding to the vessel stump will overlap the real vessel stump in the image.

As noted above, the vessel may be located in the image using the stump of the vessel as a starting point. From this starting point, for each image component (e.g. each pixel where the image is a two-dimensional image or each voxel where the image is a three-dimensional image, as described earlier) in a region surrounding the stump, the method may comprise causing the processor 102 of the system 100 to determine a measure that is indicative of the likelihood that the image component comprises part of the vessel. This measure may be referred to as a "vesselness" measure. In some embodiments, the measure may comprise a probability that the image component comprises part of a vessel. The method may then further comprise causing the processor 102 of the system 100 to locate a further portion of the vessel from the location of the stump and the determined measures. For example, in some embodiments, neighbouring components having measures above a predetermined threshold (e.g. probabilities of being part of a vessel higher than a pre-determined threshold) may be assumed to be part of the vessel.

In some embodiments, after locating the further portion of the vessel in this manner, the method for locating a further portion of the vessel may be repeated iteratively, such that for each further portion of the vessel that is located, another further portion of the vessel is located in the manner described earlier. This may comprise causing the processor 102 of the system 100 to, for each image component in a region surrounding the further portion of the vessel, determine a measure that is indicative of the likelihood that the image component comprises part of the vessel and locate another further portion of the vessel from the determined measures. In this way, the location of the vessel is identified by iteratively identifying regions that are most likely to correspond to vessels in the image.

In some embodiments, the direction in which the regions corresponding to vessels are identified in the image may be monitored. This can, for example, ensure that the location of the vessel being identified (e.g. located/traced) in the image corresponds to a direction which is compatible with the vessel being a pulmonary vessel. For example, in some embodiments, the method may be truncated and the located vessel discarded if the vessel becomes more caudal than a predefined threshold. In some embodiments, the predefined threshold is determined based on the average extent of the lung. In some embodiments, the threshold may be set to truncate the method if it is detected that the vessel being identified extends 80 mm (or approximately 80 mm) from the aortic arch as vessels extending further than this are increasingly less likely to be part of the lung. In some embodiments, the method is truncated if the vessel is found to extend more than a predetermined threshold from the stump. In some embodiments, the method is truncated if the vessel is found to extend more than 300 mm (or more than approximately 300 mm) away from the stump. In this way, the method is prevented from identifying vessels in cardiac regions, ensuring that the identified vessel corresponds to a vessel in the lung.

In some embodiments, the measure indicative of the likelihood that image components comprise part of the vessel can be determined from the density profile of the image components in the region surrounding the stump. For example, an edge or boundary of a vessel may be determined if there is a change (for example, a sudden change, that occurs across two or three image components) in the density values of neighbouring image components, indicating a boundary between the vessel and other tissue. Thus, image components may be determined to more likely belong to a vessel if their density values correspond to the density of vessels, than if they have a different density to the vessel density. In some embodiments, the edge of a vessel may be determined by casting search rays from the centre of a known portion of a vessel and measuring the radii at which the density drops below a value associated with vessels. In this sense, image components within the measured radii are determined to have a higher likelihood of belonging to a vessel, than image components that lie outside the measured radii. In some examples therefore, an image component will be assigned a higher probability of belonging to a vessel if it has a similar value (e.g. pixel/voxel value) to image components that are known to be parts of vessels than an image component that has a different value (e.g. pixel/voxel value) to neighbouring image components that are known to belong to a vessel.

In some embodiments, the measure indicative of the likelihood that each image component comprises part of the vessel is calculated based on eigenvalues of a matrix of second spatial derivatives in a multi-resolution scale space. For example, the image of the lung may be convolved with different width kernels (e.g. Gaussian kernels) to create a multi-resolution scale space. Each image of the multi-resolution scale space may then be processed to calculate the eigenvalues of a matrix of second spatial derivatives of the image components in the image. For each image location, the minimum of the second largest eigenvalue is determined, for each resolution image. The measure indicative of the likelihood that each image component comprises part of the vessel may be determined by the negative magnitude of this minimum (and set to zero for positive values of this minimum).

In some embodiments, the measure indicative of the likelihood that each image component comprises part of the vessel may further take account of the locations of other anatomical structures in the image. For example, image components known to correspond to bones (e.g. ribs) may be assigned a measure of zero, indicating that there is no probability that these image components correspond to a vessel. Alternatively or additionally, the method may be truncated if a further portion of the vessel intersects a region of the image that is known to comprise bone. The skilled person will appreciate that the locations of bones (e.g. rib bones) can be determined using any of the segmentation techniques described herein.

It will be appreciated that the methods of calculating the measure indicative of the likelihood that an image component comprises part of the vessel that are provided herein are examples only and the skilled person will be aware of other possible methods of determining a measure that is indicative of the likelihood that the image component comprises part of the vessel.

In some embodiments, in block 202, the processor may be caused to locate a vessel in the image with a diameter that is less than a predefined threshold diameter. For example, locating vessels with diameters less than a predetermined threshold may be prioritised. In this way, for example, large mediastinal vessels are excluded and the impact of smaller vessels typical for the lung (and typical of hyperdense lung tissue, such as hyperdense parenchyma in the lung) are located.

Figure 3:
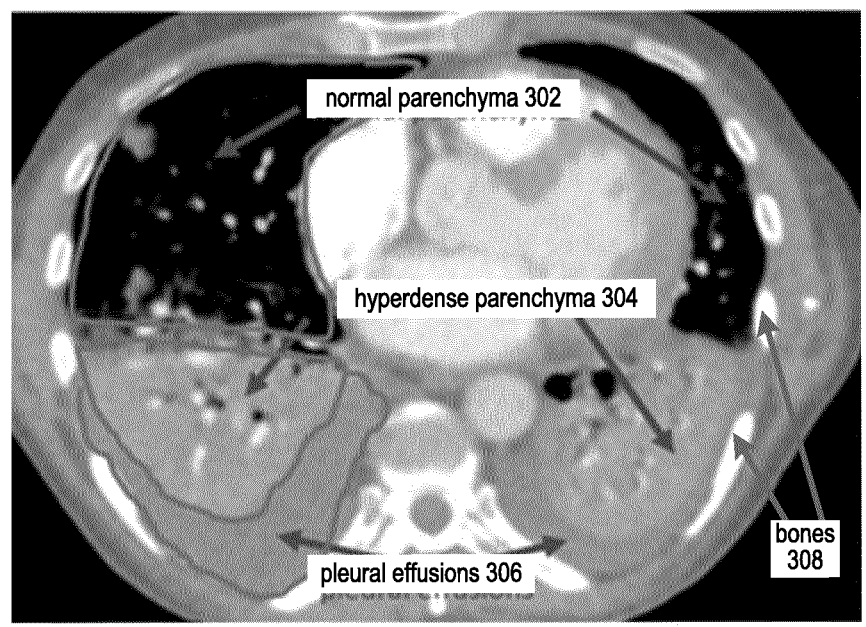
FIG. 3 shows a horizontal cross-sectional image of a lung.
Figure 4:
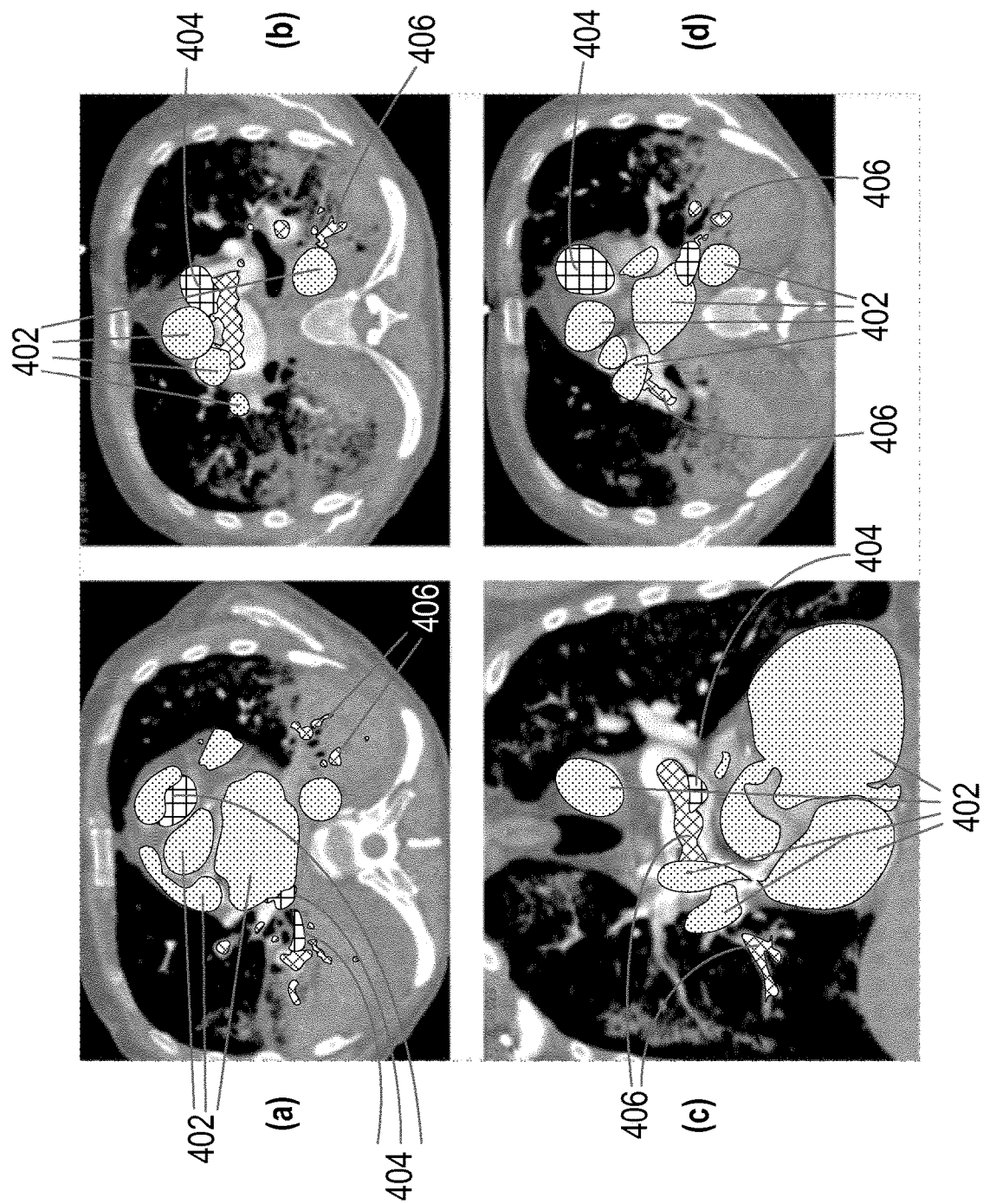
FIGS. 4a-d illustrate an example of locating a vessel in an image according to an embodiment.
Figure 5:
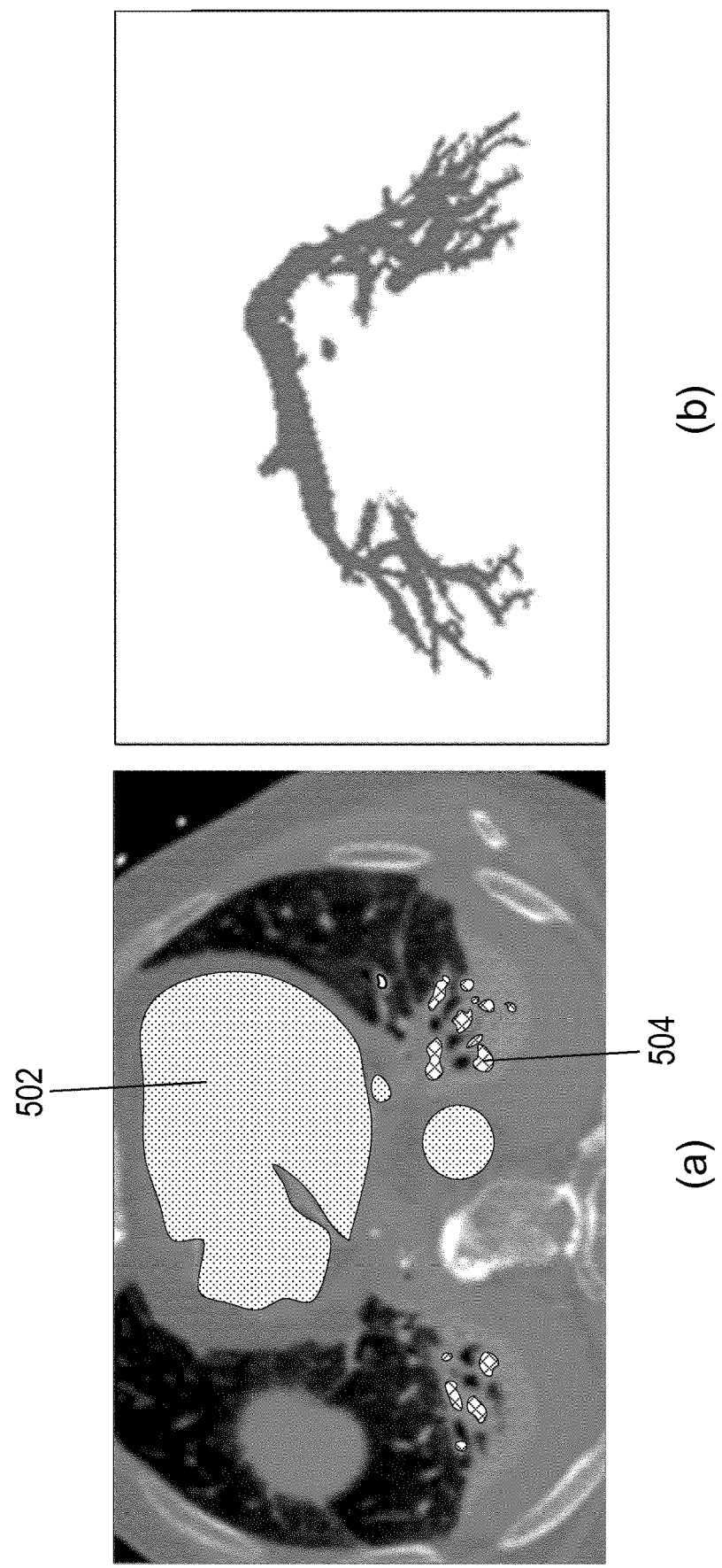
FIGS. 5a and 5b illustrate further examples of locating vessels in an image according to an embodiment.

FIGS. 3-5 illustrate some of the aforementioned methods of determining a location of a vessel in an image at block 202 of FIG. 2.

FIG. 3 shows an example image of a lung according to an embodiment. In this example embodiment, the image of the lung comprises a two-dimensional image of the lung or, more specifically, a horizontal cross-sectional slice through the lung. The image of the lung comprises regions of normal density parenchyma 302, hyperdense parenchyma 304, pleural effusions 306 and rib bones 308.

FIG. 4 illustrates an embodiment where locating a vessel in the image (at block 202 of FIG. 2) comprises segmenting the image to locate one or more portions of the heart, identifying from the segmentation a stump of a vessel and locating the vessel in the image using the stump as a starting point. FIGS. 4 a-d illustrate four horizontal cross-sections through a three-dimensional image of a chest cavity. The heart has been segmented using the methods outlined above with respect to block 202 of FIG. 2. FIGS. 4 a-d thus show the segmented portions of the heart 402, the stumps of vessels (as identified from the segmentation) 404 and the vessels themselves (located using the stumps as starting points) 406.

FIG. 5a shows another segmentation of the heart and the associated vascular structure. Segmented heart portions are labelled 502 and vessels (for example, veins) 504. A three-dimensional illustration of the determined vascular structure is shown in FIG. 5b, showing the branched structure.

An advantage associated with locating vessels according to some of the aforementioned embodiments that use a portion of a vessel that leaves the heart as the starting point is that regions of the image that comprise hyperdense lung tissue can be determined (or identified) without segmenting the lung itself. As was noted above, one of the difficulties associated with automated diagnosis of lung tissue is that lung segmentation is often inaccurate for diseased lungs, as the diseased areas do not fit to standard lung models (as can be appreciated from the image of a diseased lung shown in FIG. 3). Thus, by starting from a vessel that leaves the heart (which may be less affected by disease) instead of the lung, these problems can be avoided and the efficiency of the method improved.

Thus, as described above, a vessel is located in the image of the lung. Turning back to FIG. 2, at block 204, once the vessel is located at block 202, the set of instructions cause the processor 102 of the system 100 to determine a density of lung tissue in a region of the image that neighbours the located vessel. In some embodiments, the region of the image that neighbours the located vessel can comprise a plurality of connected image components (e.g. image components bordering one another) that are adjacent to the located vessel. The plurality of connected components can be, for example, a plurality of connected pixels where the image is a two-dimensional image or a plurality of connected voxels where the image is three-dimensional image. In some embodiments, the region of the image that neighbours the located vessel can be adjacent to the vessel or a portion of the vessel. For example, the region of the image that neighbours the located vessel may be a polygon such as a square or rectangle (in two-dimensional images) or a polyhedron such as a cuboid (for three dimensional images) that lies next to the vessel. In some embodiments, the causing the processor 102 of the system 100 to determine a density of lung tissue in a region of the image that neighbours the located vessel can comprise causing the processor 102 to determine the density of lung tissue in a region of the image that surrounds the located vessel. For example, the region of the image that neighbours the located vessel may wrap around the vessel in an approximately cylindrical or tube-shaped manner. The region of the image that neighbours the located vessel may therefore encompass all image components within a minimum threshold radius of the vessel. In some examples, the threshold radius can be 20 mm (or approximately 20 mm). In some embodiments, the region of the image that neighbours the located vessel may be shaped according to neighbouring features in the image. For example, a region of the image that neighbours the located vessel may be defined as comprising all pixels within a predefined radius of the vessel with values above a minimum threshold value.

Figure 6:
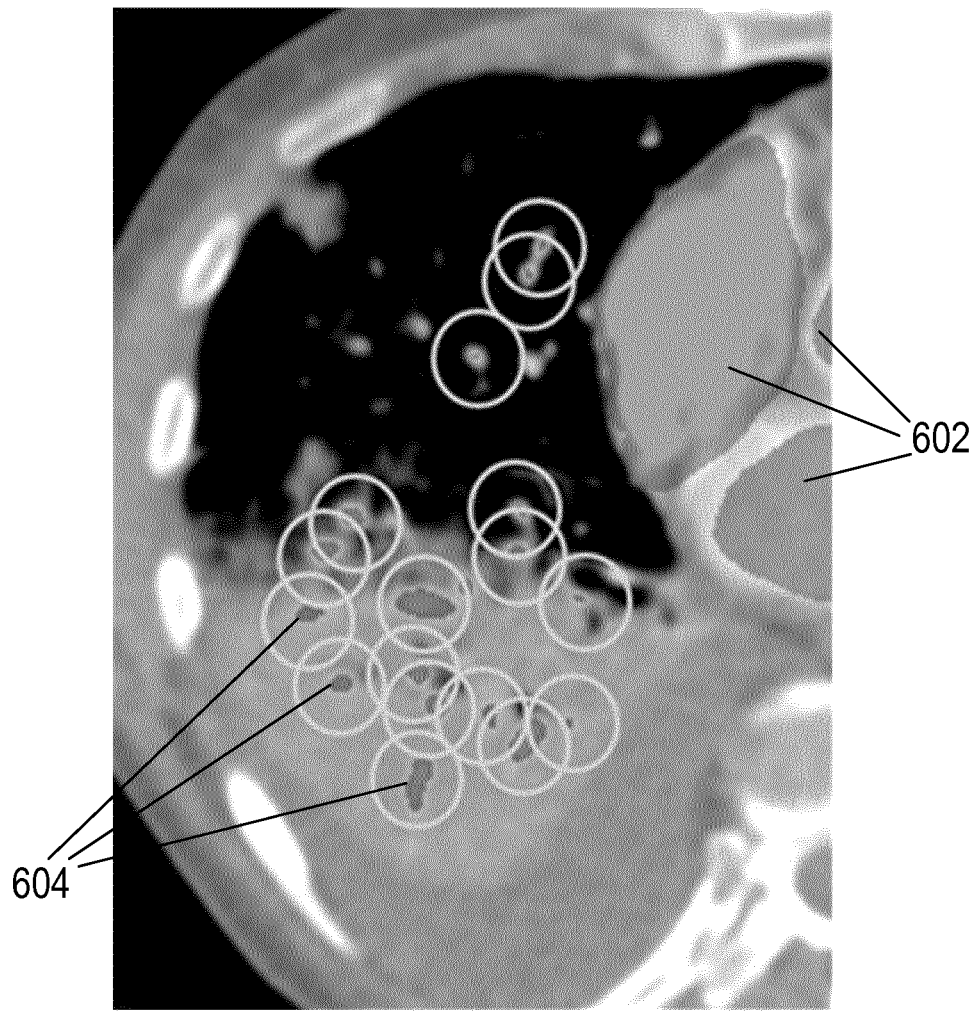
FIG. 6 illustrates regions of hyperdense lung tissue in an image of a lung, according to an embodiment.

FIG. 6 shows an example of different regions of the image that neighbour the located vessel in a computed tomography (CT) image of a lung. The image shows portions of the heart 602 and located vessels 604. Cylindrical regions (corresponding to the circles in FIG. 6) have been defined around each located vessel 604 to illustrate the regions of the image that neighbour the located vessels 604 that are candidate regions for hyperdense lung tissue and thus are the regions in which the density of lung tissue is determined (at block 204 of FIG. 2).

In some embodiments, determining a density of lung tissue in a region of the image that neighbours the located vessel (at block 204 of FIG. 2) may comprise calculating an average density in the region of the image that neighbours the located vessel. For example, the density may be determined from the mean, median or modal value of the values of the image components in the determined region. In some embodiments, determining a density of lung tissue in a region of the image that neighbours the located vessel comprises determining a distribution of density values of the image components in the region. For example, in some examples, a histogram of density values of the image components in the region is determined. In some embodiments, the determined density comprises a measure associated with the distribution of density values of the image components in the region. For example, the determined density may comprise the standard deviation of the values of the image components in the region of the image that neighbours the located vessel.

Generally, the density of the lung tissue in each image component (e.g. each pixel of a two-dimensional image or each voxel of a three-dimensional image) of a region in the image that neighbours a located vessel may be determined from the value associated with the image component using a predetermined relationship. As noted earlier, computed tomography (CT) scanners are calibrated onto the Hounsfield scale with reference to water, which has a value of 0 HU, and to air, which has a value of −1000 HU. The density D (in units of g/mm$^3$) is computed from the Hounsfield number V (in units of HU) as D=(V+1000)/1000. The person skilled in the art will be familiar with the Hounsfield scale and how this scale relates to other measures of density.

Returning back to FIG. 2, at block 206, the set of instructions when executed by the processor 102 of the system 100 cause the processor 102 to, based on the determined density of the lung tissue in the region of the image that neighbours the located vessel, determine whether the region of the image comprises hyperdense lung tissue. Thus, the determined density of the lung tissue in the region of the image that neighbours the located vessel is used to determine whether the region of the image comprises hyperdense lung tissue.

In some embodiments, block 206 of FIG. 2 can comprise comparing the determined density of the lung tissue in the region of the image that neighbours the located vessel to a threshold density. In some embodiments, a region may be determined to comprise hyperdense lung tissue where the density of the lung tissue in the region is greater than an average density of aerated lung tissue. In some embodiments, the average density of aerated lung tissue is taken to be −800 (or approximately −800) Hounsfield units (HU). Thus, in some examples, the region is determined to contain hyperdense lung tissue if the average density of the region is −800 (or approximately −800) Hounsfield units (HU).

In some embodiments where a distribution of density values is determined at block 204 of FIG. 2, block 206 of Figure can comprise comparing the determined density distribution to a predetermined density distribution of heathy lung tissue. Block 206 may further comprise determining whether the determined density distribution is shifted with respect to the predetermined density distribution of healthy lung tissue. For example, if the determined density distribution is shifted (e.g. the peak of the distribution is shifted) to higher densities compared to the predetermined density distribution of healthy tissue, then this may indicate that the region comprises hyperdense lung tissue. If the determined density distribution is centred on 0 HU, then this may indicate that the hyperdensity is in fact a pleural effusion, rather than hyperdense lung tissue. In this way, density distributions can be used to remove false-positive pleural effusions from genuine samples of hyperdense lung tissue.

In some embodiments, hyperdense regions may be prioritised according to the diameter of the associated vessel, so as to exclude large mediastinal vessels and to emphasise the impact of smaller vessels typical for the lung. This can be achieved by applying a weighting to each image component when calculating the density distribution. The weighting for a specific image component in the density calculation may be computed, for example, from the inverse of the estimated distance of the image component from the centre of the vessel. This weighting is therefore higher for small vessel radii, than large vessel radii and tends to zero for radii above an upper limit.

Although not illustrated in FIG. 2, in any of the embodiments described herein, where the region is determined to comprise hyperdense lung tissue, the set of instructions, when executed by the processor 102 of the system 100, may further cause the processor 102 to identify a medical condition associated with the hyperdense lung tissue. In some embodiments, a medical condition may be identified using the distribution of density values in the region of the image that neighbours the located vessel. In some embodiments, the medical condition can be any one or more of: atelectasis or pneumonia. For example, different medical conditions have different density profiles. In some examples, the density profiles may have different peak values in the histogram, or different width histograms. The method may therefore further comprise comparing a histogram of density values of the image components in the region to a histogram of density values associated with lung tissue affected by the medical condition. In this way, the method 200 of FIG. 2 may not only be used to determine the location(s) of hyperdense lung tissue in the image, but also to diagnose the cause of the hyperdense lung tissue.

Figure 7:
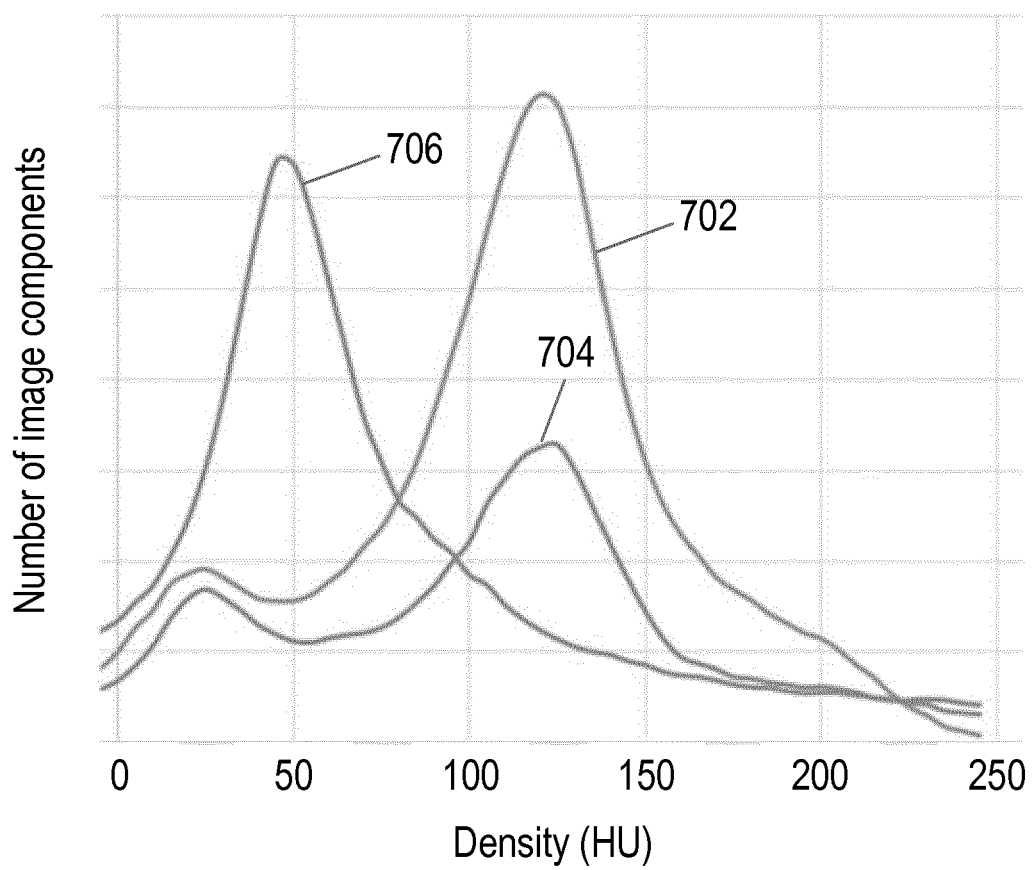
FIG. 7 illustrates lung density histograms associated with atelectasis and pneumonia.

FIG. 7 shows example density histograms from hyperdense lung tissue regions of three different lungs, which can be used to identify a medical condition associated with the hyperdense lung tissue. The histograms show distinctly different peaks, each peak corresponding to a different disease (e.g. different diseases produce different average density tissue). In this case, the three peaks signifying atelectasis 702, 704 versus pneumonia 706. Although specific examples of medical conditions have been provided, the skilled person will appreciate that the techniques described herein are not limited to those medical conditions, but can be used to diagnose or distinguish between any medical condition(s) having distinctive density profiles.

Although not illustrated in FIG. 2, in any of the embodiments described herein, the locations of other anatomical structures may be taken into account. For example, the set of instructions, when executed by the processor 102 of the system 100 may further cause the processor 102 to determine the location of a bone (such as a rib, vertebrae, or any other bone, or any combination of bones) in the image and determine that hyperdense lung tissue is absent in the region of the image that neighbours the located vessel, if the region overlaps the determined location of the bone.

The locations of bones may generally be taken into account at various different stages of the method 200 of FIG. 2. For example, the method 200 of FIG. 2 may further comprise a pre-processing block whereby one or more bones are segmented in the image. The locations determined in the segmentation may then be masked during the subsequent blocks of the method 200 of FIG. 2, to ensure that regions comprising bones are not subsequently falsely determined to comprise hyperdense lung tissue. In another example, bones may be taken into account in a post-processing step of the method 200 of FIG. 2 whereby the locations of the regions that are determined to comprise hyperdense lung tissue are compared to the locations of bones in the image and the regions that are determined to comprise hyperdense lung tissue, which overlap with the locations of bones, may be discarded. In this way, any false-positive detections of hyperdense lung tissue due to bone tissue may be mitigated.

Although not illustrated in FIG. 2, in any of the embodiments described herein, the set of instructions, when executed by the processor 102 of the system 100, may further cause the processor 102 to determine a location of a hyperdense region in the image and determine that the hyperdense region comprises pleural effusion if the location of the hyperdense region lies outside the region of the image that neighbours the located vessel. Thus, if hyperdense regions are located in the image by any method, including but not limited to the methods described herein, the method may further comprise the set of instructions causing the processor 102 to compare the location of the determined hyperdense region to the location of the located vessels in the image, and determining that the hyperdense region comprises a pleural effusion if the hyperdense region does not comprise any vessels. In this way, a plurality of located vessels in the image may further be used to determine the locations of pleural effusions in the image.

There is thus provided an improved system and method for determining regions of hyperdense lung tissue in an image of a lung, which overcome existing problems.

There is also provided a computer program product comprising a computer readable medium, the computer readable medium having computer readable code embodied therein, the computer readable code being configured such that, on execution by a suitable computer or processor, the computer or processor is caused to perform the method or methods described herein. Thus, it will be appreciated that the disclosure also applies to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to the embodiments described herein.

It will also be appreciated that such a program may have many different architectural designs. For example, a program code implementing the functionality of the method or system may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system configured for determining regions of hyperdense lung parenchyma in an image of a lung, the system comprising:
   a memory comprising instruction data representing a set of instructions;
   a processor configured to communicate with the memory and to execute the set of instructions, wherein the set of instructions, when executed by the processor, cause the processor to:
      locate a vessel in the image by locating a vessel stump and iteratively locating further portions of the vessel from the location of the vessel stump based on one or more of direction of the further portions of the vessel or distance from the vessel stump of the further portions of the vessel;
      identify a region of lung tissue to evaluate for hyperdense lung parenchyma by selecting only regions that neighbor the located vessel, wherein the neighboring regions comprise connected image components that are adjacent to the located vessel;
      determine a density of lung parenchyma in the identified region; and
      determine whether the identified region comprises hyperdense lung parenchyma based on the determined density, hyperdense lung parenchyma having a density greater than −800 Hounsfield units (HU).

2. The system as claimed in claim 1, wherein the image comprises a plurality of image components; and
   wherein the determined density of lung parenchyma in the region is a distribution of density values of the image components in the region.

3. The system as claimed in claim 2, wherein the distribution of density values comprises a histogram of density values of the image components in the region.

4. The system as claimed in claim 1 wherein, if the region is determined to comprise hyperdense lung parenchyma, the set of instructions, when executed by the processor, further cause the processor to:

identify a medical condition associated with the hyperdense lung parenchyma using a distribution of density values in the region of the image that neighbors the located vessel.

5. The system as claimed in claim 1, wherein the set of instructions, when executed by the processor, further cause the processor to:

determine a location of a bone in the image; and determine that hyperdense lung parenchyma is absent in the region if the region overlaps the determined location of the bone.

6. The system as claimed in claim 1, wherein the set of instructions, when executed by the processor, further cause the processor to:

determine a location of a hyperdense region in the image; and determine that the hyperdense region comprises pleural effusion if the location of the hyperdense region lies outside the region of the image that neighbors the located vessel.

7. The system as claimed in claim 1, wherein a region is determined to comprise hyperdense lung parenchyma where the density of the lung parenchyma in the region is greater than an average density of aerated lung parenchyma.

8. The system as claimed in claim 7, wherein the average density of aerated lung parenchyma is approximately −800 Hounsfield units (HU).

9. The system as claimed in claim 1, wherein causing the processor to locate a vessel in the image comprises causing the processor to:

segment the image to locate one or more portions of the heart;

identify, from the segmentation, the vessel stump, wherein the vessel stump corresponds to a portion of the vessel that leaves the heart; and locate the vessel in the image using the stump as a starting point.

10. The system as claimed in claim 9, wherein the image comprises a plurality of image components and wherein causing the processor to locate a vessel in the image comprises causing the processor to:

for each image component in a region surrounding the vessel stump, determine a measure that is indicative of the likelihood that the image component comprises part of the vessel; and locate a further portion of the vessel from the location of the vessel stump and the determined measures.

11. The system as claimed in claim 10, wherein causing the processor to locate the vessel in the image further comprises causing the processor to iteratively, for each further portion of the vessel that is located:

for each image component in a region surrounding the further portion of the vessel, determine a measure that is indicative of the likelihood that the image component comprises part of the vessel; and locate another further portion of the vessel from the determined measures.

12. The system as claimed in claim 1, wherein the processor is caused to locate a vessel in the image with a diameter that is less than a predefined threshold diameter.

13. A computer-implemented method for determining regions of hyperdense lung parenchyma in an image of a lung, the method comprising:

locating a vessel in the image by locating a vessel stump and iteratively locating further portions of the vessel from the location of the vessel stump based on one or more of direction of the further portions of the vessel or distance from the vessel stump of the further portions of the vessel;

identifying a region of lung tissue to evaluate for hyperdense lung parenchyma by selecting only regions that neighbor the located vessel, wherein the neighboring regions comprise connected image components that are adjacent to the located vessel;

determining a density of lung parenchyma in the identified region of the image; and determining whether the identified region comprises hyperdense lung parenchyma based on the determined density, hyperdense lung parenchyma having a density greater than −800 Hounsfield units (HU).

14. A non-transitory computer readable medium having computer readable code embodied therein, the computer readable code being configured such that, on execution by a suitable computer or processor, causes the computer or processor to:

locate a vessel in the image by locating a vessel stump and iteratively locating further portions of the vessel from the location of the vessel stump based on one or more of direction of the further portions of the vessel or distance from the vessel stump of the further portions of the vessel;

identify a region of lung tissue to evaluate for hyperdense lung parenchyma by selecting only regions that neighbor the located vessel, wherein the neighboring regions comprise connected image components that are adjacent to the located vessel;

determine a density of lung parenchyma in the identified region of the image; and determine whether the identified region comprises hyperdense lung parenchyma based on the determined density, hyperdense lung parenchyma having a density greater than −800 Hounsfield units (HU).

* * * * *